(12) United States Patent
Callaghan et al.

(10) Patent No.: US 10,737,084 B2
(45) Date of Patent: *Aug. 11, 2020

(54) DRAINAGE DEVICES AND METHODS FOR USE

(71) Applicants: The Board of Trustees of the Leland Stanford Junior University, Palo Alto, CA (US); LXS, LLC, Palo Alto, CA (US)

(72) Inventors: Matthew J. Callaghan, Stanford, CA (US); Joelle A. Faulkner, Toronto (CA); Kevin Zi Jun Chao, Palo Alto, CA (US); John Avi Roop, Menlo Park, CA (US); Stephen Arie Leeflang, Sunnyvale, CA (US); Christian Scott Eversull, Palo Alto, CA (US)

(73) Assignees: The Board of Trustees of the Leland Stanford Junior University, Stanford, CA (US); LXS, LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,422

(22) Filed: Jun. 19, 2017

(65) Prior Publication Data
US 2017/0354812 A1    Dec. 14, 2017

Related U.S. Application Data

(63) Continuation of application No. 13/179,452, filed on Jul. 8, 2011, now Pat. No. 9,682,223, which is a
(Continued)

(51) Int. Cl.
*A61M 39/02* (2006.01)
*A61B 5/0215* (2006.01)
(Continued)

(52) U.S. Cl.
CPC ....... *A61M 39/0247* (2013.01); *A61B 5/0215* (2013.01); *A61B 5/036* (2013.01);
(Continued)

(58) Field of Classification Search
CPC ... A61B 5/0215; A61B 5/036; A61B 5/14539; A61B 5/41; A61B 5/413; A61B 5/418;
(Continued)

(56) References Cited

U.S. PATENT DOCUMENTS

5,391,143 A * 2/1995 Kensey ............... A61M 27/002
604/28
9,682,223 B2 * 6/2017 Callaghan ............ A61B 5/0215
(Continued)

*Primary Examiner* — Brandy S Lee
(74) *Attorney, Agent, or Firm* — William A. English; Vista IP Law Group LLP (57) ABSTRACT

Devices and methods for draining excess lymph fluid are disclosed. The device can be fixed to the blood vessel adjacent to the thoracic duct. The device can have a port for withdrawing lymph fluid exiting the thoracic duct. The device can have a cannula and/or subcutaneous port to draw the lymph fluid away from the thoracic duct and reduce hemostatic pressure in the lymphatic system.

13 Claims, 8 Drawing Sheets

Related U.S. Application Data continuation-in-part of application No. PCT/US2010/000073, filed on Jan. 12, 2010.

(60) Provisional application No. 61/204,893, filed on Jan. 12, 2009.

(51) Int. Cl.

| | |
|---|---|
| *A61B 5/03* | (2006.01) |
| *A61B 5/145* | (2006.01) |
| *A61B 5/00* | (2006.01) |
| *A61M 25/01* | (2006.01) |
| *A61F 2/06* | (2013.01) |
| *A61F 2/82* | (2013.01) |
| *A61M 27/00* | (2006.01) |
| *A61M 25/00* | (2006.01) |

(52) U.S. Cl.
CPC ............ *A61B 5/14539* (2013.01); *A61B 5/41* (2013.01); *A61B 5/413* (2013.01); *A61M 25/01* (2013.01); *A61B 5/418* (2013.01); *A61F 2/064* (2013.01); *A61F 2/82* (2013.01); *A61F 2002/061* (2013.01); *A61M 27/002* (2013.01); *A61M 2025/0057* (2013.01); *A61M 2025/0197* (2013.01); *A61M 2039/0258* (2013.01); *A61M 2039/0276* (2013.01); *A61M 2039/0291* (2013.01); *A61M 2039/0297* (2013.01); *A61M 2202/0405* (2013.01); *A61M 2230/208* (2013.01)

(58) Field of Classification Search
CPC ...... A61F 2002/061; A61F 2/064; A61F 2/82; A61M 2025/0057; A61M 2025/0197; A61M 2039/0258; A61M 2039/0276; A61M 2039/02; A61M 2202/0405; A61M 25/1011; A61M 1/3653; A61M 27/002; A61M 1/3659; A61M 2025/1015; A61M 2025/1052; A61M 2205/3317; A61M 1/3496; A61M 1/367; A61M 1/3609; A61M 2205/3306; A61M 2205/3331; A61M 2230/208; A61M 1/34; A61M 1/3639; A61M 1/3655; A61M 2025/0002; A61M 2205/10; A61M 2205/3334; A61M 2230/207; A61M 2230/30; A61M 25/0026; A61M 25/10; A61M 27/008; A61M 1/00; A61M 1/1008; A61M 1/1029; A61M 1/1086; A61M 1/125; A61M 2025/1022; A61M 2025/1097; A61M 2205/3303; A61M 2205/3344; A61M 2205/8206; A61M 2210/12; A61M 25/00; A61M 25/0017; A61M 25/003; A61M 25/10184; A61M 1/101; A61M 1/1018; A61M 1/1034; A61M 1/122; A61M 1/369; A61M 2025/0036; A61M 2025/0681; A61M 2025/1013; A61M 2205/32; A61M 2205/33; A61M 2205/36; A61M 2205/366; A61M 25/002; A61M 25/0032; A61M 25/0108; A61M 25/02; A61M 25/0662; A61M 5/44; A61M 2025/0004; A61M 2025/0062; A61M 2025/0063; A61M 2205/0205; A61M 25/0009; A61M 25/0013; A61M 25/0043; A61M 25/0054; A61M 25/0136; A61M 25/0138; A61M 25/0147; A61M 25/09; A61M 1/1012; A61M 1/1039; A61M 1/3656; A61M 2025/0037; A61M 2025/0086; A61M 2025/009; A61M 2039/0291; A61M 2039/0297; A61M 2205/3379; A61M 2205/3592; A61M 2205/50; A61M 2205/505; A61M 2205/80; A61M 2210/1082; A61M 2210/1089; A61M 2230/06; A61M 2230/201; A61M 2230/42; A61M 2230/63; A61M 25/0074; A61M 25/0084; A61M 25/01; A61M 25/04; A61M 31/007; A61M 37/0069; A61M 39/0247; A61M 39/24; A61M 5/14; A61M 5/14276; A61M 5/1452; A61M 5/1723; A61M 5/178

See application file for complete search history.

(56) References Cited

U.S. PATENT DOCUMENTS

| | | | |
|---|---|---|---|
| 2006/0100658 A1* | 5/2006 | Obana | A61F 2/013 606/200 |
| 2008/0140000 A1* | 6/2008 | Shuros | A61N 1/36007 604/96.01 |
| 2008/0269718 A1* | 10/2008 | Wiener | A61B 17/3417 604/506 |

\* cited by examiner

Figure 1A

NOT INVENTION

Figure 1B

NOT INVENTION

DRAINAGE DEVICES AND METHODS FOR USE

CROSS REFERENCE TO RELATED APPLICATIONS

This application is a continuation of co-pending application Ser. No. 13/179,452, filed Jul. 8, 2011, issuing as U.S. Pat. No. 9,682,223, which is a continuation-in-part of International Application No. PCT/US2010/000073, filed Jan. 12, 2010, which claims priority to U.S. Provisional Application No. 61/204,893, filed 12 Jan. 2009. The entire disclosures of these applications are expressly incorporated by reference herein.

BACKGROUND OF THE INVENTION

1. Field of the Invention

The present device and method relate generally to accessing, draining, and monitoring the lymphatic system. This device can be used to treat volume overload in heart failure, pulmonary edema, after surgical procedures and in other disease states in which interstitial volume removal or lymphatic sampling are of use.

2. Description of the Related Art

Congestive heart failure affects 5.5 million Americans and is a leading cause of death in the U.S. Each year, over one million patients are hospitalized for heart failure and 90% of these are diagnosed with volume overload. Volume overload in patients with heart failure is an acute manifestation of a chronic decrease in cardiac performance such that the heart is unable to pump and circulate the volume of blood returning from the venous system. As a result, blood accumulates in the pulmonary and peripheral tissues. A common and potentially life threatening consequence of decompensated heart failure is pulmonary edema, which presents as shortness of breath and poor oxygenation, both indicative of fluid accumulation in lung tissues and small airways. If left untreated, patients are at risk for hypoxic arrest and death. Peripheral swelling and venous distension are also common, although not as life threatening.

In most cases, patients with this presentation are known to be suffering from a chronic heart condition and are taking prescribed diuretic medications to control their volume status. The sudden onset of volume overload is due to either a miscalculation in salt and fluid intake or poor medication compliance on the part of the patient, or a result of a worsening heart condition, renal impairment, or resistance to diuretic medications.

Once diagnosed, the initial therapy for volume overload in decompensated heart failure is intravenous diuresis. Despite the use of intravenous diuretics in 90% of overload patients, the average hospital admission time is 4.3 days and over half of those discharged will return within six (6) months with the same diagnosis. It is suggested that the high readmission rate is due to inadequate volume reduction during their previous admission. Furthermore, approximately 30% of chronic heart failure patients on diuretics will develop resistance or renal failure as a result of their medication and require more invasive and higher risk therapies to control their volume status. These interventions include mechanical ventilation with positive pressure, central venous ultrafiltration, or hemodialysis.

The physiology of pulmonary edema suggests fluid accumulation in the small airways is the direct result of increased hydrostatic pressure in the surrounding capillaries, which leak first into the interstitial space between the capillary bed and the airway. This extracellular space is composed of protein matrices and small lymphatic channels designed specifically to accommodate homeostatic changes in pressure by draining any excess interstitial fluid which is not immediately resorbed by the venous capillary bed. These lymphatic channels combine as they travel towards the neck, eventually forming one large channel called the thoracic duct. The thoracic duct rejoins the systemic venous system at the lymphovenous junction, near the confluence of the left internal jugular and subclavian veins. In the case of clinically significant pulmonary edema, the hydrostatic forces generated by a failing heart quickly overwhelm the lymphatic system and blood plasma overflows into the smaller airways. In this case, the lymphatic system is limited by volume capacity and higher than expected flow pressures generated by the venous system into which the thoracic duct is draining.

The human lymphatic system has been accessed previously for the purposes of sampling and draining lymphatic fluid to treat blood cancers, transplant rejection, pancreatitis and rheumatoid arthritis. These maneuvers have involved open surgery and acute cannulation of the thoracic duct in small numbers of patients with extracorporeal processing of lymphatic fluid. The majority of the fluid was returned to the patient after processing.

While the function and overloading of the lymphatic system in pulmonary edema is well documented, current therapies for volume overload focus on systemic pharmaceutical diuresis or direct drainage of the vascular compartment to filter and remove blood plasma. Therefore, there exists a need for a therapy to monitor and manage pulmonary and systemic volume overload by manipulation and drainage of the existing lymphatic system. Drainage of lymphatic fluid specifically from the thoracic duct can quickly reverse the interstitial fluid imbalance in the pulmonary tissues and offload a significant amount of peripheral volume. Furthermore, lymphatic fluid is pre-filtered and does not include red blood cells or platelets which need to be separated and returned to the patient in conventional hemodialysis and ultrafiltration.

Outside of heart failure, development of this device will provide a much needed tool to accelerate research and treatment in a range of related disease states such as cancer, HIV, organ transplant, and autoimmune disorders.

Interstitial fluid accumulation can become a critical issue in any post-operative patient and is especially concerning after heart surgery, when it is important to limit cardiac stress. In these critical care and post-surgical volume management situations, and at other times, thoracic duct drainage in at-risk patients can augment volume management and prevent overload.

Fluid in the thoracic duct contains a high percentage of circulating CD-4 lymphocytes, the target cell for HIV. In animal models, drainage and characterization of T-cells by thoracic duct drainage can answer some of the fundamental immunological questions about recirculating lymphocyte pools to help develop new vaccine and antiviral therapies.

An early method of immune suppression in organ transplantation was thoracic duct drainage. The open cannulation procedure and subsequent wound care was challenging and unsuccessful in many patients. Once immune suppressive medications became more effective, this approach was abandoned altogether.

SUMMARY OF THE INVENTION

The devices and methods described herein can enable repeated fluid communication between an internal body vessel and an extracorporeal fluid reservoir, such as a syringe. In one embodiment, the device can have a cannula or other tubular member. The cannula can enable fluid communication between the vessel and an external accessing device. The device can be in fluid communication with the vessel with or without occluding the vessel. If fluid is not being withdrawn from the cannula, the fluid in the body vessel can bypass the cannula. The device can remain in a fixed position in the vessel. The device can be secured internally, externally, or a combination thereof, to the body vessel. The cannula can be secured along the internal lumen of the body vessel by stabilizing members. The stabilizing members can support the vessel. The stabilizing members can be a single balloon, for example, positioned at the junction of the thoracic duct and the innominate vein, or two balloons, for example positioned on opposite sides of the thoracic duct port as the thoracic duct merges into the innominate vein. The stabilizing members can include anchoring hooks and/or loops. The device, such as on the outer perimeter of the balloon, can have an ingrowth matrix to promote endothelial growth into the device to fix the device to the surrounding tissue, such as the vessel wall.

The device can be anchored in and/or to the vessel without occluding the vessel, for example, even in very small vessels. The device can be able to puncture the vessel wall. The cannula can create the path for fluid flow external to the vessel and/or a means to access the vessel. The device can include an access port. The device can include a pressure sensor. The device can include valves to control fluid flow. The device can include a reservoir to hold fluid that has traveled through the cannula.

The device may be used to remove lymphatic fluid in patients experiencing pulmonary edema. When the patient is not experiencing pulmonary edema, for example, the lymphatic fluid may flow through the vessel past the cannula. When the patient is experiencing higher than normal flow of lymphatic fluid, for example, the fluid may activate an entrance mechanism to the cannula and/or signal that the device needs to be accessed. When the device is accessed, fluid may be withdrawn from the lumen through the cannula. When the patient is experiencing pulmonary edema or at the onset of pulmonary edema, the device may be accessed.

The device can allow fluid communication between a lymphatic vessel and an external reservoir. For example, the device can open the wall of (i.e., access) the thoracic duct. The device can drain fluid from the lymphatic vessel. For example, the cannula can drain fluid from the thoracic duct. The device can drain lymphatic fluid from the lymphatic system, for example, when the patient becomes fluid-overloaded or suffers from congestive heart failure. The device can help prevent and/or treat congestive heart failure and pulmonary edema, for example, by drainage of the lymphatic system.

The device may access blood vessels. The device may access central venous or arterial vessels. The device may withdraw fluid from the vessels. The device may withdraw blood from blood vessels. The device may store the fluid in a reservoir. The device may access the portal vein. The device may access the proximal portal vein, before the triad. The device may measure the pressure in blood vessels. The device may measure portal hypertension.

The device can be placed in a stationary fashion in a blood vessel adjacent to the thoracic duct. The device can have a port positioned adjacent to the opening of the thoracic duct into the innominate, internal jugular or subclavian vein or the junction thereof. The device can be used to passively or actively (e.g., by applying negative pressure) withdraw lymphatic fluid as it exits the thoracic duct into the adjacent vein. The device's port, which is adjacent to the thoracic duct, can be in fluid communication with a drainage cannula and/or subcutaneous port that can be used to withdraw the lymph fluid.

The device can be deployed adjacent to the opening of the thoracic duct into the innominate vein. The device can be deployed in a minimally invasive fashion, such as through a subclavian or other intravascular delivery. The thoracic duct opening can be identified using a visualization method. For example, the thoracic duct opening can be identified using an intravenous ultrasound (IVUS) probe. The IVUS probe can be in a liquid-inflatable (e.g., saline) balloon. The thoracic duct opening can be identified using a sensor to identify changes in the intravascular fluid composition. For example, lymph fluid is typically more alkaline than blood, so a pH sensor can be deployed into the innominate vein to locate the peak pH when in the vicinity of the thoracic duct to locate the opening of the thoracic duct into the innominate vein. A combination of methods, such as those disclosed herein, can be used to identify the thoracic duct opening to coordinate placement of the device.

A user may singularly or repeatedly access the device, for example, to sample lymph fluid for monitoring of triglycerides, lymphocytes, or lymphatic protein content in chronic conditions such as hyperlipidemia, cancer, immune deficiencies or auto-immune disorders.

A user may singularly or repeatedly access the device, for example, to sample lymph fluid and/or for reduction of fluid volume in patients experiencing or at risk for volume overload, and/or pulmonary edema and/or chronic heart failure and/or acute exacerbation of chronic heart failure.

Periodic monitoring of lymphocyte antigen, for example, after solid organ transplant, can provide an early warning of graft rejection and a more accurate indication of the level of immune suppression. For example, lymph fluid can be withdrawn through the device and analyzed after a high risk graft or transplant procedure. For example, the device can be implanted and lymph fluid can be removed through the device and analyzed for graft rejection after a heart, lung, kidney, skin, liver, or small intestine transplant or graft. The device can provide a safe and minimally invasive method of lymphatic access, which could be provided with a transcutaneous catheter. Routine drainage of sensitized lymphocyte subpopulations could help prevent or rescue an acute episode of rejection.

As a clinical modality, catheter drainage of the thoracic duct through the device can remove the lymph fluid to deplete large numbers of CD-4 cells (for example, CD-4$^+$ T cells). Combining drainage with conventional pharmacological therapy to decrease the infection rate in remaining CD-4 cells can promote a shift towards a virus-free state and represents an intriguing alternative to current treatment for HIV or other infectious diseases with similar modalities.

In accordance with another embodiment, a method is provided for reducing interstitial volume in a patient using a device comprising a tubular member that includes placing a distal end of the tubular member into a patient's venous system such that the distal end is located adjacent the thoracic duct; draining fluid from the lymphatic system via the thoracic duct through a lumen of the tubular member to reduce fluid volume within the patient's body; and discontinuing draining fluid when the fluid volume is sufficiently reduced.

Optionally, the method may also include resuming draining fluid from the lymphatic system via the thoracic duct when the pressure in the thoracic duct exceeds a predetermined threshold, e.g., about twenty five millimeters of Mercury pressure (25 mm Hg).

In accordance with yet another embodiment, a method is provided for decreasing lymphocyte numbers in a patient affected by autoimmune or infectious disease using a device comprising a tubular member that includes placing a distal end of the tubular member into a patient's venous system such that the distal end is located adjacent the thoracic duct; and draining fluid from the lymphatic system via the thoracic duct through a lumen of the tubular member.

Optionally, the method may also include analyzing lymphocytes in the fluid drained from the thoracic duct to identify a subset of lymphocytes; removing the identified subset of lymphocytes from the fluid; and returning the fluid into the patient's body after removing the identified subset of lymphocytes. In another option, the method may include analyzing lymphocytes in the fluid drained from the thoracic duct; processing the fluid outside the patient's body; and returning the fluid into the patient's body.

In accordance with still another embodiment, a method is provided for evaluating interstitial fluid status within a patient's body that includes placing a distal end of a tubular member into a patient's venous system such that the distal end is located adjacent the thoracic duct; measuring pressure within the tubular member distal end to approximate lymphatic pressure within the thoracic duct; providing an alert outside the patient's body when the measured pressure within the tubular member exceeds a predetermined threshold; and removing interstitial fluid from the thoracic duct via the tubular member until the measured pressure falls below the predetermined threshold.

For example, the methods herein may include substantially isolating the thoracic duct from the venous system using the device such that flow from the thoracic duct is directed through the tubular member to drain fluid from the lymphatic system.

In one embodiment, the distal end of the tubular member may be introduced into the venous system until the distal end is advanced into the thoracic duct. Optionally, negative pressure may be applied to the lumen to increase fluid flow from the thoracic duct through the cannula.

In another embodiment, the device may include a subcutaneous access port coupled to the tubular member for accessing fluid drained through the tubular member.

In addition or alternatively, the device may include one or more balloons on the tubular member, and the method may include inflating the one or more balloons to maintain the tubular member in a substantially fixed position relative to the thoracic duct.

In yet another embodiment, the device may include a Nitinol frame, and the method may include expanding the frame to maintain the tubular member in a substantially fixed position relative to the thoracic duct. For example, the device may include an elastic material on the Nitinol frame, e.g., a silicone component, to substantially isolate the thoracic duct from the venous system and maintain the tubular member in a substantially fixed position relative to the thoracic duct.

In accordance with yet another embodiment, a device is provided for accessing fluid from a thoracic duct of a patient via the patient's venous system that includes a tubular member comprising a distal end sized for introduction into the patient's venous system adjacent the thoracic duct; one or more features on the distal end for substantially isolating the thoracic duct from the venous system; and a lumen for withdrawing interstitial fluid from the thoracic duct. For example, the distal end is sized to fit inside the subclavian vein of the patient, and wherein the tubular member has a length sufficient to extend to the thoracic duct from a percutaneous access point in the left subclavian vein.

In one embodiment, the one or more features may include a Nitinol frame and a low durometer silicone component or other elastic member including an opening communicating with the lumen. For example, the Nitinol frame may include two flexible members extending from the tubular member and supporting the silicone component. Optionally, the silicone component may be bonded to the Nitinol frame, the silicone component being sufficiently flexible to stretch to substantially seal the thoracic duct outlet.

Other aspects and features of the present invention will become apparent from consideration of the following description taken in conjunction with the accompanying drawings.

SUMMARY OF THE DRAWINGS

It will be appreciated that the exemplary apparatus shown in the drawings are not necessarily drawn to scale, with emphasis instead being placed on illustrating the various aspects and features of the illustrated embodiments.

FIG. 3A' illustrates a variation of the drainage device in which the intraluminal member has the shape of a hemi-cylinder.

FIG. 3B' illustrates a variation of the device of FIG. 3B.

DETAILED DESCRIPTION

The devices and methods disclosed herein enable removal of fluid from a vessel within the body. For example, the device can be placed in a lymph or blood vessel to remove lymph fluid from the body. The removal of lymph fluid can reduce the hemostatic pressure in the lymphatic system, reducing symptoms of congestive heart failure.

Figure 1A:
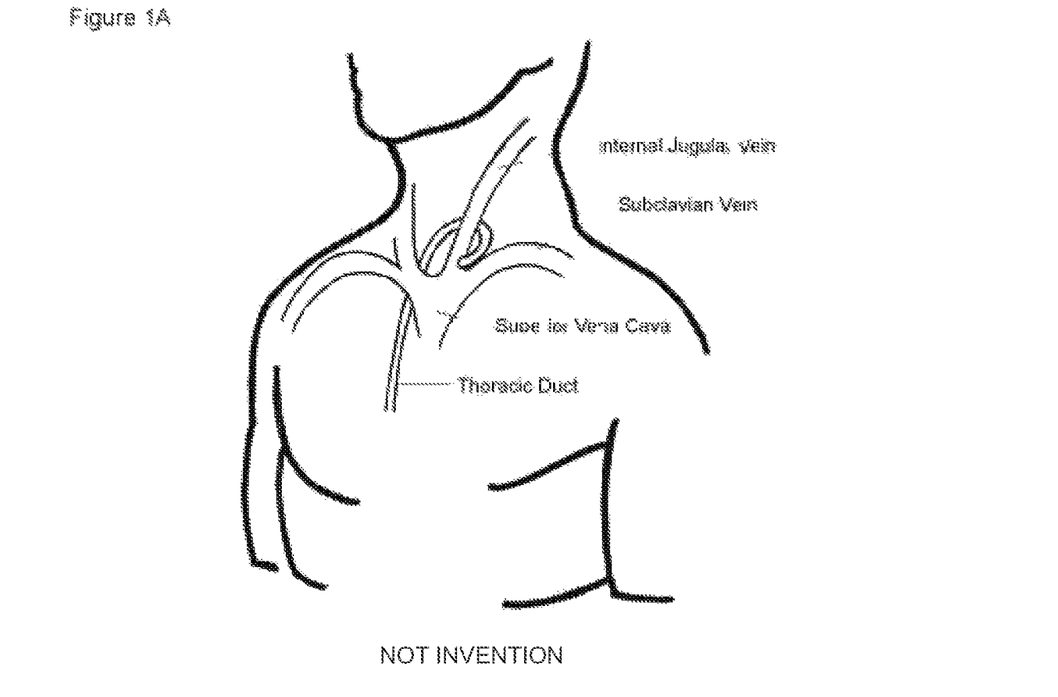
FIG. 1A illustrates the major venous anatomy of the chest and neck and the location of the thoracic duct.
Figure 1B:
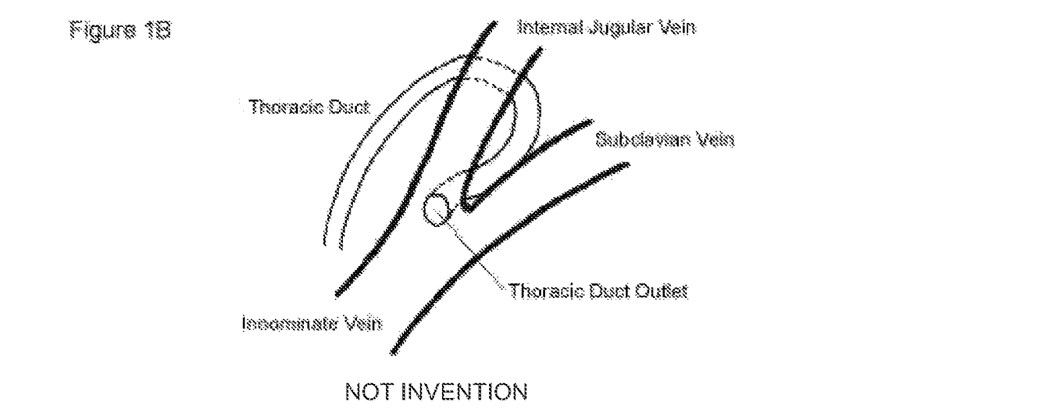
FIG. 1B illustrates the location of the thoracic duct outlet as it enters the central venous system.

The device can access the lumen of a body vessel, for example, a lymphatic vessel and/or blood vessel. Fluid can drain from the vessel into the device. For example, the device can be in fluid communication with the thoracic duct or central veins (e.g., subclavian vein, internal jugular vein, superior vena cava, and innominate vein) shown in FIG. 1A and FIG. 1B. The device can reduce the pressure within the lumen by draining and removing excess fluid. The excess fluid can be stored in the device. The excess fluid can flow through a port and removed percutaneously. The device could treat pulmonary edema, for example, by reducing the pressure in the interstitial space, such as around the alveoli.

The device can have a cannula, intraluminal and extraluminal members, and one or more of the following: access port, sensor, pressure sensor, flow meter, reservoir.

Fluid overload, or hypervolemia, is a medical condition where there is too much fluid in the blood. The total body fluid can be too much for the heart to pump. Under normal physiological conditions, this would result in fluid building up in the tissue. The thoracic duct outlet would typically allow lymph fluid to drain from the thoracic duct into central venous system, but when the blood pressure in the innominate vein becomes too high compared to the lymph fluid pressure in the thoracic duct, the lymph fluid cannot properly drain through the thoracic duct outlet and may prevent proper draining of the lymph system and exit the lymphatic system in a pathological manner.

Figure 2A:
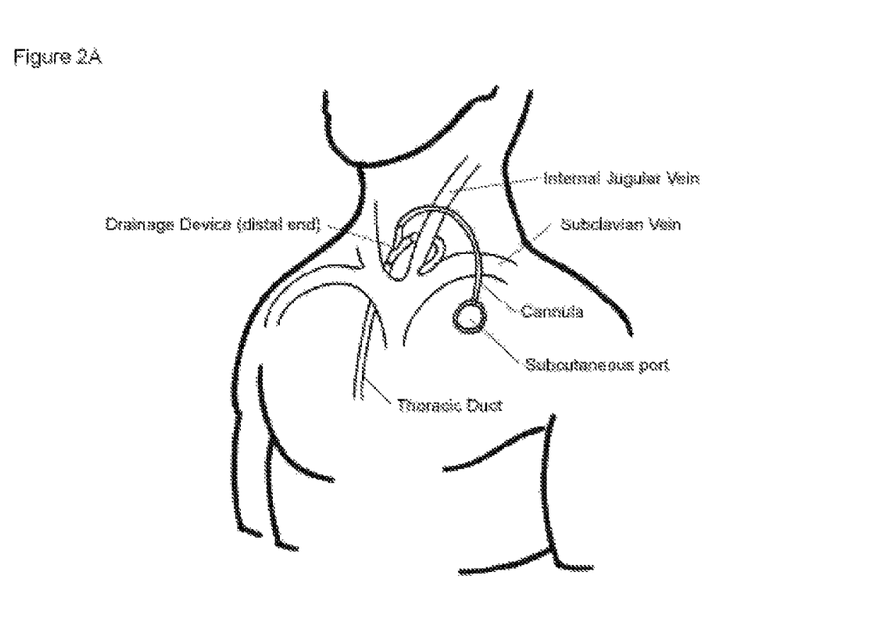
FIG. 2A illustrates a variation of the drainage device placed in the thoracic duct with a subcutaneous port under the skin of the left chest wall.

FIG. 2A illustrates a variation of the drainage device placed inside the thoracic duct. The draining device can be in fluid communication with a tube or cannula. The drainage device can be connected to and in fluid communication with a subcutaneous port, for example, via the cannula. The drainage device can be placed anywhere along the cervical thoracic duct. The cannula can drain fluid from the draining device to an internal or external reservoir or port, such as the subcutaneous port. The subcutaneous port can be drained, for example, by occasional access by a percutaneous needle.

Figure 2B:
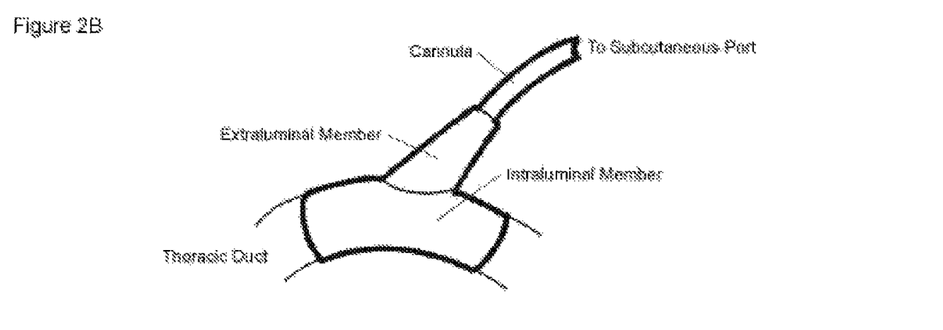
FIG. 2B illustrates a variation of the drainage device in deployed in a thoracic duct.

FIG. 2B illustrates that the drainage device may include intraluminal and extraluminal members. The intraluminal and/or extraluminal members can be cylindrical and/or conical in shape.

The intraluminal member of the device can be inserted into the thoracic duct lumen. The intraluminal member can be hollow. The intraluminal member can be in fluid communication with the body lumen, for example, the thoracic duct. The intraluminal member can be capable of carrying fluid from the body lumen. The intraluminal member can be in continuous or discontinuous (i.e., temporary, or sequentially repeating off and on by automatic or manual control) fluid communication with the body lumen. The cannula can access the vessel without significantly occluding the vessel. The intraluminal member can occupy some of the cross sectional area of the vessel the intraluminal member is accessing. The intraluminal member can occupy a small amount of the cross sectional area of the blood vessel. The extraluminal member of the device can be in fluid communication with both the intraluminal member and the cannula. The extraluminal member can cross the full thickness of the thoracic duct wall.

The drainage device can remain in a given position in the vessel by hooks and barbs (not shown). The drainage device can maintain the position without hooks and barbs. The extraluminal member may be secured to the cannula. The cannula can hold the drainage device in place. The exterior surface of the drainage device, such as along the intraluminal member, can have an ingrowth matrix configured to promote tissue ingrowth to anchor the drainage device to the surrounding tissue, such as the endothelium or intima of the blood vessel.

The intraluminal and extraluminal members may be rigid. The intraluminal and extraluminal members may be flexible. The intraluminal and/or extraluminal members can have soft grafts and/or reinforcing self-expandable or balloon-expandable metal or polymer stents. Portions of the intraluminal or extraluminal members may be more rigid, for example, the extraluminal member. Portions of the intraluminal or extraluminal members may be more flexible, for example, the intraluminal member.

The device can enable indirect access to the vessel. The device can be accessed by a needle on a syringe, and the device can include an access port. The access port can be in fluid communication with the vessel. The access port can be connected to the cannula and the cannula can be in fluid communication with the vessel.

Figure 2C:
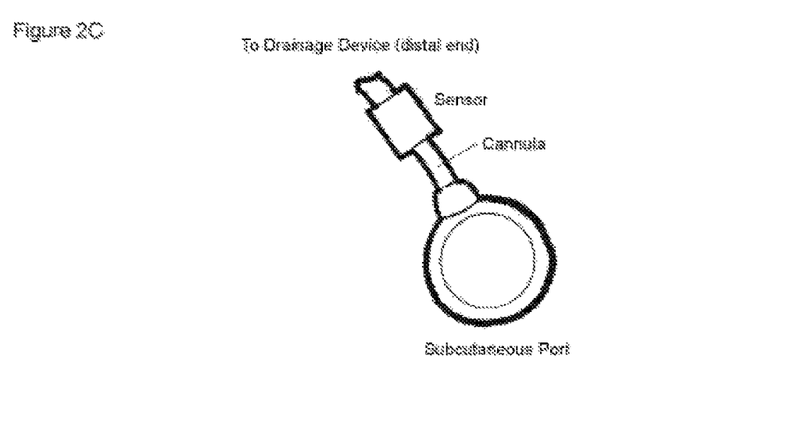
FIG. 2C illustrates a variation of a subcutaneous port and in-line sensor.

FIG. 2C illustrates that the access port can be a subcutaneous access port. The access port may include a gel port. The gel port can be self-sealing, for example, re-sealing after removal of the access device, such as a needle. The access port may be in fluid communication with the cannula.

The device may include one or more sensors. The sensors may include pressure sensors, pH sensors, ultrasound sensors, and/or volume sensors. The sensors may detect temperature and/or changes in temperature and/or impedance and/or changes in impedance and/or chemical composition of the fluid (such as acidity and alkalinity) and/or changes in chemical composition of the fluid. The sensors may detect pressure and/or changes in pressure in the vessel and/or in the cannula and/or in the device. The sensors may detect flow volume and/or changes in flow volume in the cannula and/or in the vessel and/or in the device. FIG. 2C shows that a sensor may be connected to the cannula between the intraluminal member and the subcutaneous access port. The sensor may be in fluid communication with the vessel, for example the thoracic duct.

The sensor may have a means to signal the patient to high pressure. The sensor may signal when drainage of fluid is necessary. For example, the sensor may be in communication with an external device. The sensor may signal the external device. The external device may notify the patient.

The sensor may enable a physical deformation of some component of the device at a specified threshold. For example, the sensor may be a pressure sensor. The pressure sensor may be comprised of a valve and a chamber. The valve may allow fluid to pass into a reservoir only at a certain pressure. The reservoir may expand when it has fluid. The expansion may be detectable by the patient and/or by physical exam.

Figure 3A:
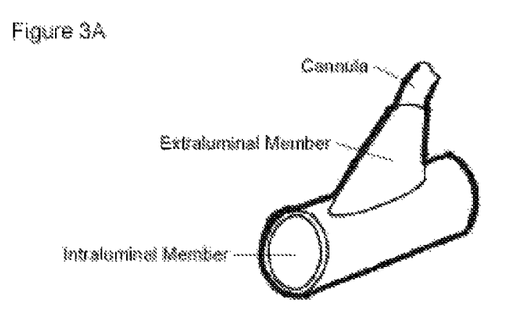
FIG. 3A illustrates a variation of the drainage device in which the intraluminal member has the shape of a closed cylinder.

FIG. 3A shows that the intraluminal member can be tubular or cylindrical. FIG. 3A' illustrates that the intraluminal member can have a semi-cylindrical or partially tubular structure where the halves of the tube, as measured from the center of the base of the cannula, are identical. When implanted in a vessel, the intraluminal member can promote laminar flow through the vessel. The intraluminal member can have a smooth surface, for example on the surface facing the vessel into which the member is implanted. The intraluminal member can aid in flow of fluid through the vessel.

Figure 3B:
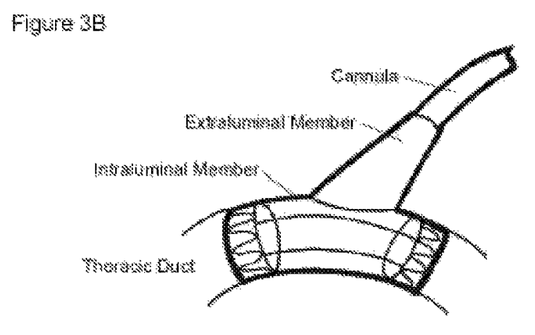
FIG. 3B illustrates a variation of the device deployed in a thoracic duct in which the intraluminal member has the shape of an incomplete cylinder.

FIGS. 3B and 3B' illustrate that the intraluminal member can be or have a self-expanding (i.e., elastically deformable) or balloon-expanding (i.e., plastically deformable) metal, plastic, or biodegradable wireframe or stent.

The device may be delivered to a vessel lumen over guidewires in separate parts. Some or all members may be expandable. Some or all members may have two configurations.

A guidewire may be used to help place the device. The guidewire may be inserted trans-abdominally. The guidewire may be advanced into the lymphatic system. The guidewire may be advanced up the lymphatic system, with the flow of lymphatic fluid, towards the thoracic duct. The same or a second guidewire may puncture the thoracic duct. The guidewire may be advanced towards the skin. An incision may be made in the chest. The incision may be made until the guidewire is able to be advanced to the skin. The cannula and/or an access port may be loaded on the guidewire. The access port may be inserted into the body and connected to the cannula.

Figure 4A:
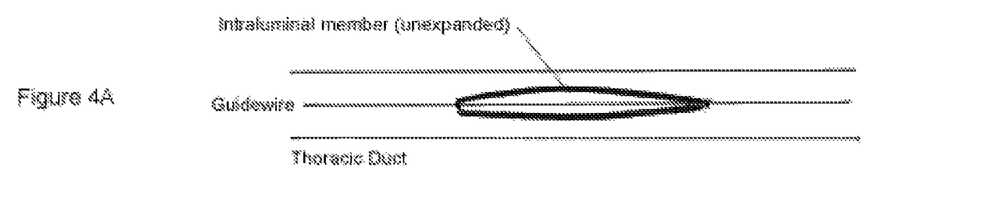
FIGS. 4A through 4D illustrate a variation of a method for delivery of a two-piece intra-ductal device.

FIGS. 4A through 4D illustrate that the device can be implanted in the thoracic duct. FIG. 4A illustrates that the device may be placed over a guidewire. The guidewire could be placed from the proximal lymphatic system using standard interventional radiology techniques. For example, the guidewire could be placed trans-abdominally. The cysterna chyli could be cannulated and a guidewire could be advanced in the lymphatic system. The guidewire could be advanced until it is at the thoracic duct. The cannula may be expanded once in the desired position. The cannula may be expanded in the thoracic duct. As another example, a vein, such as the internal jugular vein, could be cannulated with a hollow needle. The guidewire could be advanced into the junction of the thoracic duct to the venous system, then into the lymphatic system. This could be achieved with a curved-tip wire. Once in the correct position, the device could be deployed. Once the device is in the correct position the device could be expanded. The device could be expanded using a balloon, for example.

Figures 4B, 4C:
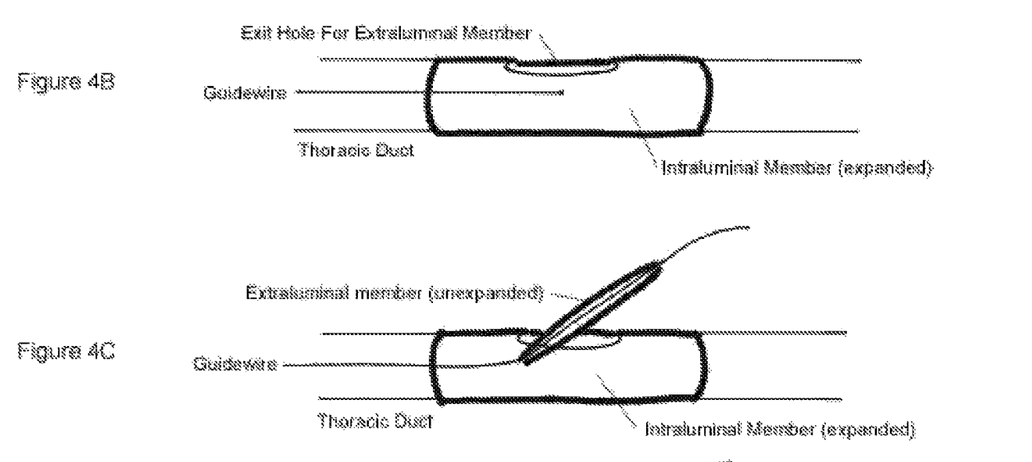
Figure 4D:
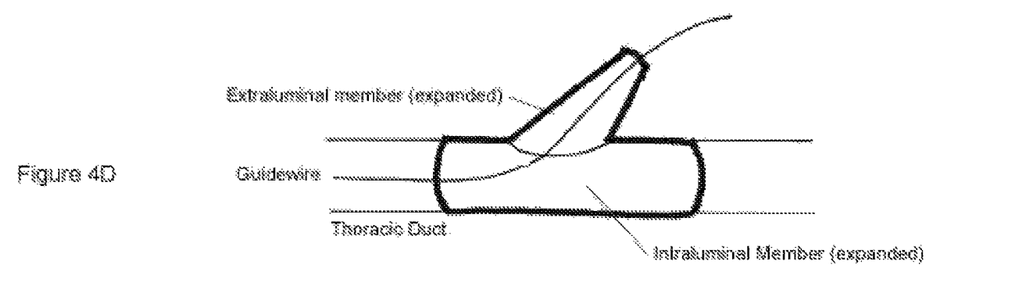

FIG. 4A shows that the intraluminal member may have a compressed configuration. The intraluminal member can be delivered over a guidewire from the distal end of the vessel. FIG. 4B shows that the intraluminal member may have a second, expanded configuration. The intraluminal member may have an aperture in its expanded formation for inserting and connecting the extraluminal member. FIG. 4C shows the extraluminal member can be delivered in a compressed configuration over a guidewire from the distal vessel. The guidewire can be passed through the exit hole in the intraluminal member. The extraluminal member can be passed through the exit hole in the intraluminal member over the guidewire. FIG. 4D shows that the extraluminal member can be expanded and connected to the intraluminal member. The cannula may be connected to the stabilizing members after implantation.

Figure 5A:
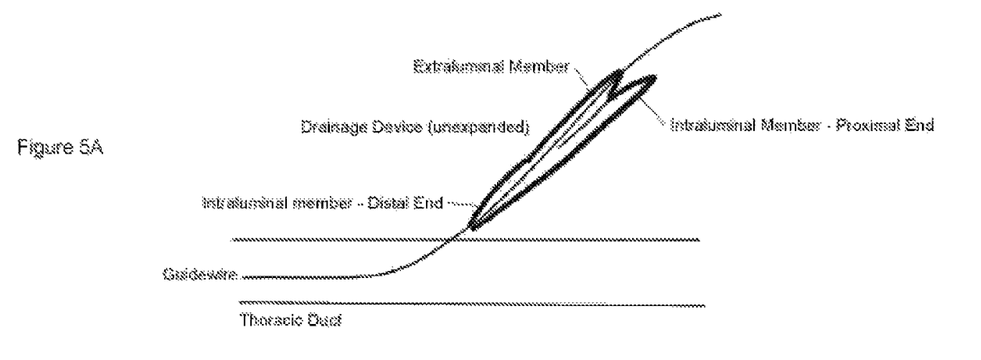
FIGS. 5A through 5C illustrate a variation of a method for delivery of a one-piece intra-ductal device.
Figure 5B:
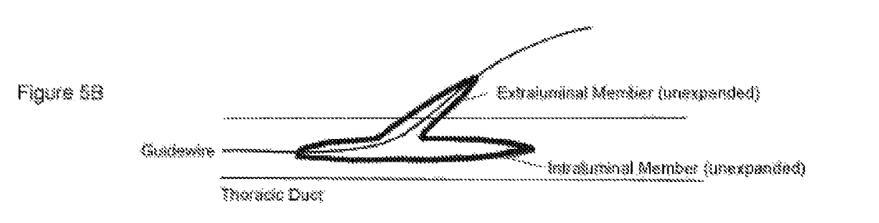
Figure 5C:
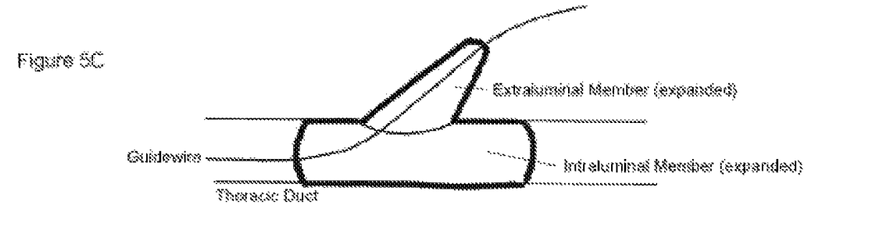

FIGS. 5A through 5C illustrate that the cannula and the stabilizing members can be part of a unitary body. The cannula and the stabilizing members can all be part of a unitary body with no seams between components.

FIG. 5A illustrates that the device can be delivered over a guidewire to the target vessel as a unitary body. In FIG. 5A, the device can be delivered to the vessel from a proximal location outside the vessel. In FIGS. 5B and 5C, the device can be radially expanded once the device has been positioned inside the thoracic duct.

The device and/or the access points to the vessel can be detectable using a visualization technology, for example ultrasound. Fluid from the vessel can be withdrawn through the drainage device by another device, for example, a needle.

The drainage device can be accessed by any number of other devices. The accessing devices may be capable of transporting fluid, and/or measuring pressure. For example, access can entail percutaneous cannulation of the device by a needle. Access can include access of the cannula and/or access of another member of the device. For example, access can include percutaneous cannulation of a subcutaneous access port of the device.

The cannula connected to the drainage device may include one or more valves. The valves may be pressure activated. For example, fluid pressure in the vessel lumen may open the valve. Fluid flow above normal physiological flow can open the valve. Once open, fluid can flow up the cannula. This may signal the patient. The signal may be physical. For example, the fluid may cause the access port to deform in a way that is detectable to the patient. The device can have a valve in the cannula that controls access to a reservoir. The valve may selectively open when the pressure of the lymphatic fluid reaches above the normal physiological pressure of the specific patient. The valve can be a one-way valve, such that fluid may never flow back to the vessel. The valve can be a pressure valve as fluid goes from the vessel towards the tip of the cannula, but allows free flow from the tip of the cannula back towards the base of the cannula. The device may be removable. The device may be collapsible. The components may have joints. For example, the tubular stabilizing members can be magnetic, and deform if a magnetic tube is placed at the core, along the longitudinal axis. The device can be collapsed under vacuum pressure. The device can be collapsed and removed. Use of the device and/or draining the lymphatic system can be used as a step to reverse and/or treat pulmonary edema and/or volume overload and/or acute heart failure and/or chronic heart failure and/or acute exacerbation of chronic heart failure.

Access can include acute cannulation and/or a means to leave behind an implanted device. Access may include trans-venous access, which may include trans-jugular, subclavian and/or femoral. Access may include access through soft tissue, which may include transcutaneous, which could include abdominal access and/or access through thoracic structures and/or access by way of and/or through nuchal structure.

Access may be aided by imaging modalities. Imaging modalities may include ultrasound, fluoroscopy, x-ray, magnetic resonance, computed tomography, direct vision, and/or magnified vision.

The lymphatic system may include the thoracic duct, and/or cisterna chyli and/or any vessel that carries the fluid and/or all vessels that carry the fluid.

Removal of the fluid may include draining the fluid to a reservoir inside and/or outside the body. A reservoir inside the body may include another area of the body, whether or not it is a cavity (i.e., the arms). A reservoir outside the body may include a container and/or an unenclosed area, draining the fluid to a naturally occurring and/or man-made container. Draining may be by way of continuous drainage and/or intermittent drainage, for example, draining can be activated when the pressure in the thoracic duct exceeds a predetermined amount. Such drainage can be by way of implanting a valve at the distal end of the thoracic duct; and/or by way of accessing a port; and/or by way of applying a mechanical force to the duct and/or to a lymphatic vessel and/or to the lymphatic system; and/or by way of cannulating the duct and/or a lymphatic vessel. The port can be permanently implanted.

The device may be accessed, for example, by a needle. Fluid may be withdrawn from the interior lumen, through the device. The overall fluid volume of the patient may be reduced.

Figures 6A, 6B, 6C:
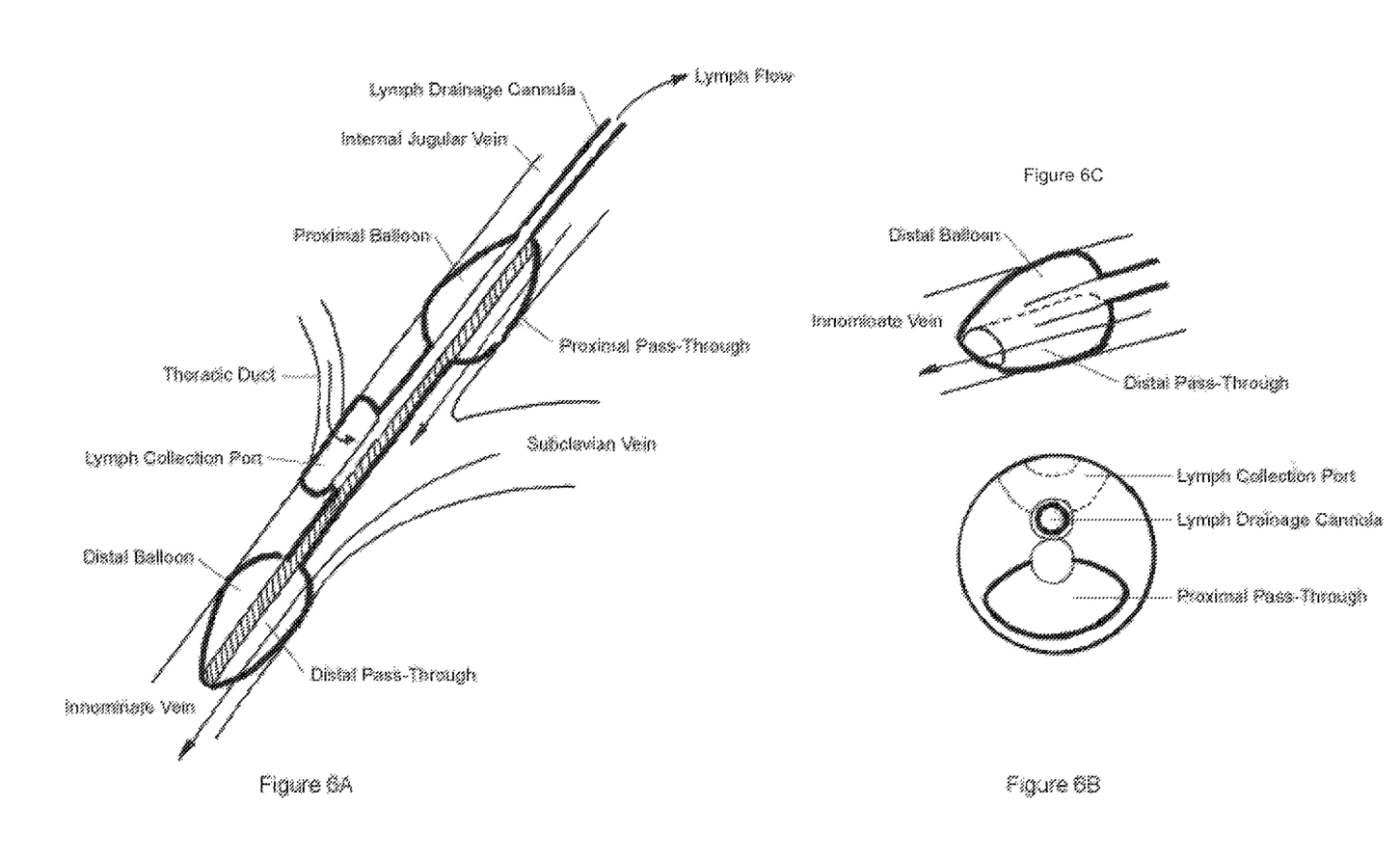
FIG. 6A illustrates a variation of the device deployed in the central venous system in opposition to the thoracic duct outlet.
FIG. 6B is an end view of the device of FIG. 6A.
FIG. 6C is a close-up of the distal end of the device of FIG. 6A.

The device may reside in the central venous system. The device may occlude or cover the outlet of the thoracic duct in the central venous system. The device may seal permanently or temporarily against the outlet of the thoracic duct. The device can fluidly isolate the thoracic duct outlet port from the venous system. For example, the distal balloon and proximal balloon can be positioned on opposite sides of the thoracic duct outlet port, and the lymph collection port (e.g., an aperture or valve on in fluid communication with the lymph drainage cannula) can be placed adjacent to the thoracic duct outlet port. The device may be activated to seal against the thoracic duct outlet only when drainage is required. FIG. 6A illustrates a variation of the device which seals against the thoracic duct using inflatable balloons. The device may allow for venous blood to pass through it when the balloons are inflated. FIG. 6B illustrates the pass-through lumen of the inflated balloons.

Figure 7:
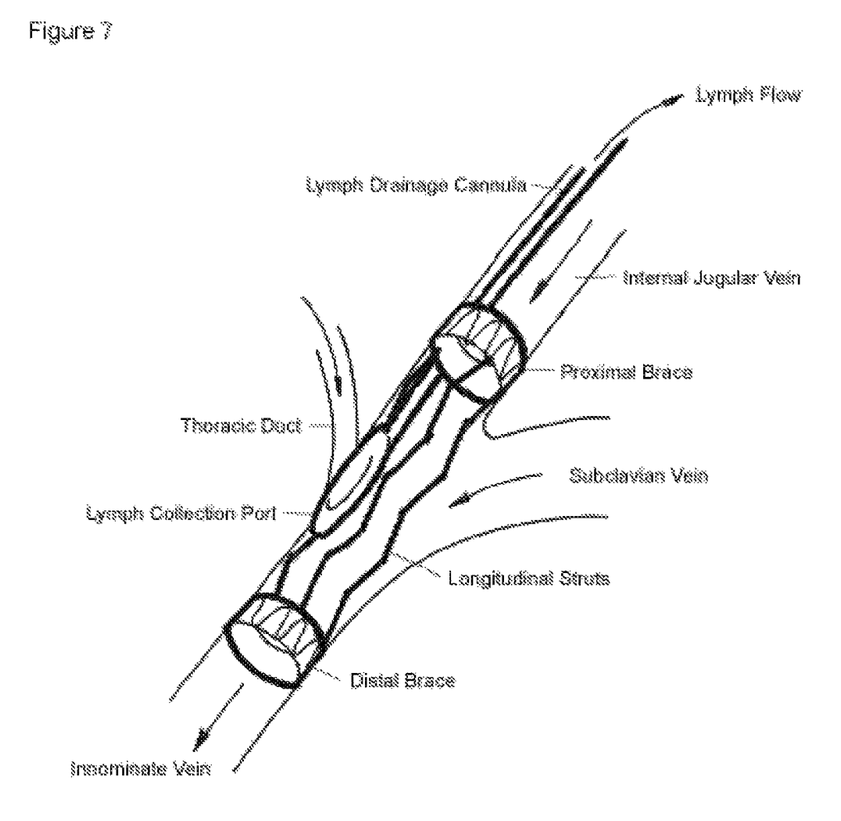
FIG. 7 illustrates a variation of the device deployed in the central venous system in opposition to the thoracic duct outlet.

The device in the central venous system may be comprised of a self-expanding metallic structure. The structure may be assembled from one piece or multiple parts. The device may be delivered to the central venous system over a guidewire. FIG. 7 illustrates a self-expanding central venous device deployed in opposition to the thoracic duct outlet. The device can have self-expanding Nitinol struts and braces.

Figures 8A, 8B, 8C:
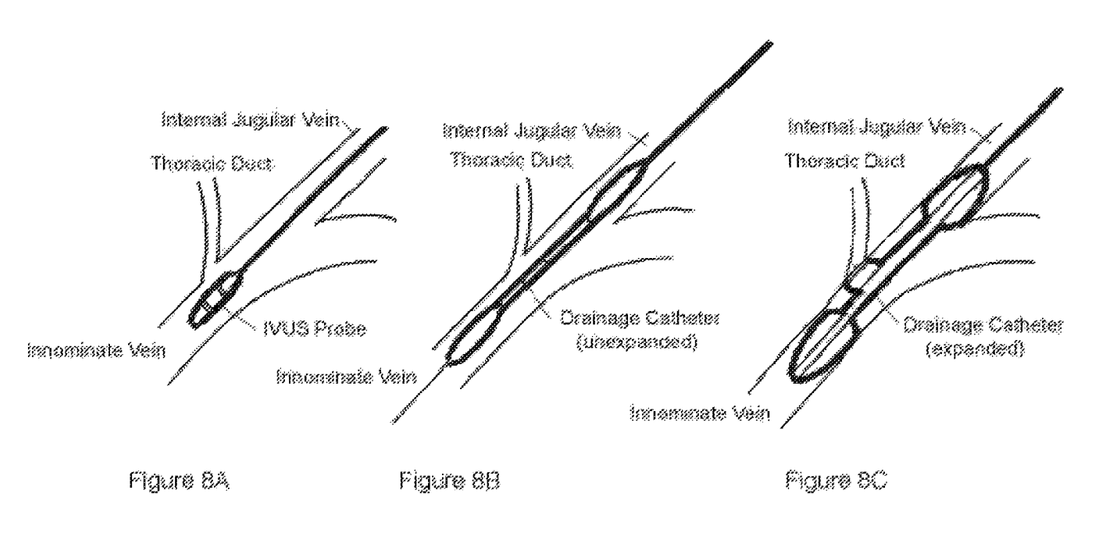
FIGS. 8A through 8C illustrate a variation of a method for delivery of a variation of the device into the central venous system using intravascular ultrasound guidance.

FIG. 8 illustrates delivering a central venous device with inflatable balloons over a guidewire. The location where the device will be deployed may be determined using an intravascular imaging modality, such as intravascular ultrasound. In FIG. 8A, an intravascular ultrasound probe can used to locate the thoracic duct outlet from the internal jugular vein. Once the location of the outlet has been determined, the intravascular ultrasound probe is removed and the balloon catheter is deployed as depicted in FIG. 8B. In FIG. 8C, the balloon catheter can be expanded in place to cover the outlet of the thoracic duct. Lymphatic fluid can be withdrawn from the cannula.

The device may be implanted. The implantation may be using a minimally invasive technique, for example, those techniques commonly used by interventional radiologists and/or interventional cardiologists. The device may enter the body at a point in the vessel more distal to the desired position. For example, the device may enter trans-abdominally into the cysterna chyli. The device may be manipulated through the vessel. Visualization aids may aid in advancing the device and/or a guidewire. For example, fluoroscopy may be used. Mechanical aids can be used to advance the device and/or a guidewire. Once in the desired position, the vessel may be punctured. Using such a technique, the complications associated with open surgery can be avoided.

Any or all elements of the device and/or other devices or apparatus described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N. V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum, and gold.

Any or all elements of the device and/or other devices or apparatus described herein, can be, have, and/or be completely or partially coated with agents and/or a matrix a matrix for cell ingrowth or used with a fabric, for example, a covering (not shown) that acts as a matrix for cell ingrowth. The matrix and/or fabric can be, for example, polyester (e.g., DACRON® from E. I. Du Pont de Nemours and Company, Wilmington, Del.), poly ester amide (PEA), polypropylene, PTFE, ePTFE, nylon, extruded collagen, silicone, any other material disclosed herein, or combinations thereof.

The device and/or elements of the device and/or other devices or apparatus described herein and/or the fabric can be filled, coated, layered, and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example, polyurethane, cellulose acetate polymer mixed with bismuth trioxide, and ethylene vinyl alcohol; lubricious, hydrophilic materials; phosphor cholene; anti-inflammatory agents, for example, non-steroidal anti-inflammatories (NSAIDs) such as cyclooxygenase-1 (COX-1) inhibitors (e.g., acetylsalicylic acid, for example, ASPIRIN® from Bayer AG, Leverkusen, Germany; ibuprofen, for example, ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example, Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin E2 Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Any elements described herein as singular can be pluralized (i.e., anything described as "one" can be more than one). Any species element of a genus element can have the characteristics or elements of any other species element of that genus. The above-described configurations, elements, or complete assemblies and methods and their elements for carrying out the invention, and variations of aspects of the invention can be combined and modified with each other in any combination.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for reducing interstitial volume in a patient's body via a thoracic duct communicating with a venous system of the patient's body using a tubular member comprising a proximal end including an access port and a distal end, the method comprising:
    implanting the tubular member into the venous system such that the distal end is located adjacent the thoracic duct and the access port is accessible;
    expanding an expandable member on the distal end to isolate the thoracic duct from the venous system;
    accessing the access port using a device outside the patient's body;
    draining fluid from the thoracic duct through a lumen of the tubular member and the device to a location outside the patient's body to reduce fluid volume within the patient's body; and
    discontinuing draining fluid and removing the device from the access port when the fluid volume is sufficiently reduced,
    wherein the distal end of the tubular member is located outside the thoracic duct.

2. The method of claim 1, further comprising applying negative pressure to the lumen to increase fluid flow from the thoracic duct through the tubular member.

3. The method of claim 1, wherein the expandable member comprises one or more balloons on the distal end of the tubular member, the method further comprising inflating the one or more balloons to maintain the tubular member in a substantially fixed position relative to the thoracic duct.

4. The method of claim 1, wherein the device comprises a Nitinol frame on the distal end, the method comprising expanding the frame to maintain the distal end in a substantially fixed position relative to the thoracic duct.

5. The method of claim 1, wherein accessing the access port comprises cannulating the tubular member with the device.

6. The method of claim 1, wherein the tubular member is implanted through an incision in a chest of the patient's body.

7. The method of claim 1, wherein the device comprises a needle.

8. The method of claim 1, wherein the access port is implanted subcutaneously in the patient's body.

9. The method of claim 1, wherein the expandable member comprises one or more balloons on the distal end.

10. The method of claim 1, further comprising:
    reaccessing the access port using a device outside the patient's body; and
    draining fluid from the thoracic duct through a lumen of the tubular member and the device to a location outside the patient's body to further reduce fluid volume within the patient's body.

11. A method for decreasing lymphocyte numbers in a patient's body affected by autoimmune or infectious disease via a thoracic duct communicating with a venous system of the patient's body using a tubular member comprising a proximal end including an access port and a distal end, the method comprising:
    implanting the tubular member into the venous system such that the distal end is located adjacent the thoracic duct and the access port is accessible;
    expanding an expandable member on the distal end to isolate the thoracic duct from the venous system;
    accessing the access port using a device outside the patient's body;
    draining fluid from the thoracic duct through a lumen of the tubular member and the device to a location outside the patient's body,
    wherein the distal end of the tubular member is located outside the thoracic duct.

12. The method of in claim 11, wherein a port on the distal end of the tubular member is aligned with an outlet of the thoracic duct such that flow from the thoracic duct is directed through the tubular member to drain fluid from the thoracic duct.

13. The method of claim 11, wherein the expandable member comprises one or more balloons on the distal end of the tubular member, the method further comprising inflating the one or more balloons to maintain the tubular member in a substantially fixed position relative to the thoracic duct.

* * * * *